United States Patent [19]

Connor et al.

[11] Patent Number: 5,298,634

[45] Date of Patent: Mar. 29, 1994

[54] PROCESS FOR MAKING MALATE SALTS AND THEREBY, AMLIC ACID OR 2,2'-OXODISUCCINATES

[75] Inventors: Daniel S. Connor; Herbert C. Kretschmar, both of Cincinnati, Ohio

[73] Assignee: The Procter & Gamble Company, Cincinnati, Ohio

[21] Appl. No.: 130,928

[22] Filed: Dec. 10, 1987

[51] Int. Cl.$^5$ .................. C07D 307/02; C07C 59/245
[52] U.S. Cl. ..................... 549/485; 562/582
[58] Field of Search .................. 562/582; 549/485

[56] References Cited

U.S. PATENT DOCUMENTS 3,128,287  4/1964  Berg ........................... 260/346.8
3,635,830  1/1972  Lamberti ........................ 252/152

OTHER PUBLICATIONS

CA 101:6267t–Chemical Abstracts (1984).
F. Lloydl, Annalen, vol. 192, pp. 80–89 (1878).
Kirk-Othmer Encyclopaedia of Chemical Technology, 3rd. Ed., vol. 13, pp. 103–121 (1981); Article entitled "Hydroxy Dicarboxylic Acids".
Erickson and Alberty, J. Phys. Chem., vol. 63, pp. 705–709 (1959).
Rozelle and Alberty, J. Phys. Chem., vol. 61, pp. 1637–1640 (1957).
Bender and Connors, J. Amer. Chem. Soc., vol. 84, pp. 1980–1986 (1962).

Primary Examiner—José G. Dees
Assistant Examiner—Joseph Conrad, III
Attorney, Agent, or Firm—Michael D. Jones; Jerry J. Yetter; Kim William Zerby

[57] ABSTRACT

Near-quantitative conversion of maleate to D,L-malate is rapidly secured by heating an aqueous alkaline mixture of maleate and excess of the divalent cations calcium, magnesium or mixtures thereof in a reactor at autogenous pressures and at temperatures above reflux. The simplest raw materials for the process are maleic anhydride and calcium hydroxide. The product is secured as an unusual, typically granular solid form of the divalent metal malate salt which is very useful in processes for preparing other malate salts, malic acid, or 2,2'-oxodisuccinate laundry detergent builders.

25 Claims, No Drawings

PROCESS FOR MAKING MALATE SALTS AND THEREBY, AMLIC ACID OR 2,2'-OXODISUCCINATES

FIELD OF THE INVENTION

The present invention is a chemical process for converting maleate to malate under aqueous alkaline reaction conditions.

BACKGROUND OF THE INVENTION

Malic acid, its salts and derivatives are well-known and useful in commerce, inter alia as food acidulants.

Malic acid has been commercially available since the early 1960's; see Kirk-Othmer, Encyclopedia of Chemical Technology, 3rd Edition, 1981, Vol. 13, pages 103-119 and the art cited therein, all incorporated herein by reference. Kirk-Othmer refers to a Japanese patent which relates to the direct hydration of maleic acid at 180° C. and 1.03-1.21 MPa (150-175 psi). A commercial synthesis of R,S-malic acid is discussed in detail by Kirk-Othmer. This synthesis involves hydration of maleic or fumaric acid at elevated temperature and pressure (180°-220° C./1.4-1.8 MPa, i.e., 200 psi or above) in a titanium reactor under acidic conditions. The reaction is inefficient in that a significant amount of fumarate is generated and has to be separated from the malic acid and recycled. After a twelve-step purification process, malic acid containing less than 1% fumaric acid and less than 0.05% maleic acid is obtained. Thus, the current commercial synthesis suffers at least four serious disadvantages: first, in the inefficiency of the malic acid formation; second, high pressures are needed; third, highly corrosive acid conditions require use of a titanium reaction vessel; and fourth, elaborate and costly purification is required.

Accordingly, it will be appreciated that a simpler means for converting low-cost maleate to malate would be advantageous. The present invention provides such a process.

BACKGROUND ART

Kinetic studies on the hydration of fumarate to malate under neutral, acid and basic (sodium hydroxide) conditions have been disclosed in the art. See Rozelle and Alberty, J. Phys. Chem., Vol. 61, 1957, pages 1637-1640; Erickson and Alberty, J. Phys. Chem., Vol. 63, 1959, pages 705-709 and Bender and Connors, J. Amer. Chem. Soc., Vol. 84, 1962, pages 1980-1986. No use of multivalent metal ions is disclosed, and the studies are typically conducted in dilute aqueous solutions.

Processes for making malate in metal salt form are also disclosed in the art; see Berg, U.S. Pat. No. 3,128,287, issued Apr. 7, 1964. Berg states that the process of his invention comprises an efficient method of producing 2,2'-oxodisuccinic acid and malic acid, and further (Col. 1, lines 13-14) " . . . said process may also be employed for an efficient conversion of maleic acid to malic acid." Disclosure provided in support of this statement is as follows:

(Col. 1, lines 32-48)

The process of this invention involves the reaction of maleic acid with a hydroxide of calcium, barium, magnesium or strontium. In general this reaction is conducted by admixing maleic acid with an excess of the hydroxide in the presence of water. The reaction mixture is then heated for from about one day to about one month at temperatures ranging from about 50° C. to reflux temperatures. Naturally, the temperature range and time intervals employed may be reduced if this reaction is conducted under pressure. The reaction time will also vary with the temperature, that is, the higher the reaction temperature, the shorter the reaction time. When the aforementioned reaction has been completed, the insoluble metal salts of malic and 2,2'-oxodisuccinic acid are filtered and washed with several portions of water to remove any remaining unreacted starting materials.

See also Col. 1, lines 65-71, which state:

As indicated above, the process of this invention produces both malic and 2,2'-oxodisuccinic acid, the ratio of these products varies with the metal hydroxide employed in the process. When strontium and barium hydroxides are employed, an almost quantitive [sic] conversion of maleic to malic acid can be effected. However, the use of calcium and magnesium hydroxide in this process produces almost an equal mixture of malic and 2,2'-oxodisuccinic acids.

It is clear from the disclosure that the Berg process does not, in fact, provide a viable commercial process for converting maleic anhydride to malic acid or salts thereof; first, insofar as strontium or barium are expensive or toxic, therefore undesirable for use in making large volume food additives or laundry detergent chemicals; and second, insofar as low yields of malate are obtained using calcium or magnesium.

As will be seen from the disclosure hereinafter, the present invention eliminates these problems and secures other objects of great utility to the manufacturer of foods and other consumer products.

SUMMARY OF THE INVENTION

The present invention encompasses an improved aqueous process for converting a maleate feedstock to malate in very high yield. The product is typically an unusual granular form of calcium malate, magnesium malate or mixtures thereof, having particularly good odor and color. The process requires use of temperatures above reflux and therefore generally uses a sealed or mildly pressurized reaction vessel. High pressures are unnecessary and the reaction does not involve formation of a corrosive, acidic reaction mixture. Insofar as the product salts may simply be acidified to liberate malic acid, the invention also encompasses an improved synthesis of malate in acid form. The product of the improved malate synthesis is also exceptionally useful for making 2,2'-oxodisuccinate laundry detergent builder salts.

Thus, the invention encompasses a process for making malate by at least one step of maintaining, in a reaction vessel (preferably sealed) at a temperature of about 120° C. or above (more preferably, about 130° C. to about 220° C., most preferably about 140° C. to about 190° C.) for a time of at least 10 minutes (more preferably about 10 minutes to about 16 hours, most preferably about 30 minutes to about 6 hours), an aqueous reaction mixture comprising:

I maleate, or mixtures thereof with one or more of 2,2'-oxodisuccinate, fumarate and malate;

II divalent cations selected from calcium, magnesium and mixtures thereof; and

III sufficient hydroxide excess to render said reaction mixture alkaline;

whereby said malate is secured in yields up to and exceeding 90%, (more preferably, exceeding about 99%).

The product may readily be isolated as a solid salt form of said divalent cation component II.

A preferred embodiment of the invention uses a reaction mixture consisting essentially of the above-defined components I, II and III and water.

In another preferred embodiment, said reaction mixture comprises said components and is substantially free from sodium or potassium cations (it is however possible to have such cations present in limited amounts).

In the simplest embodiment of the process, component I is used in the form of maleic anhydride or maleic acid, and components II and III can simultaneously be provided in the form of calcium hydroxide. As illustrated in this embodiment, the process has highly preferred ranges of composition of the reaction mixture when particular calcium/maleate mole ratios and particular aqueous concentrations are used. The calcium/maleate mole ratio is generally greater than 1:1. Typically, the calcium/maleate mole ratio is at least 1.1:1, more preferably greater than about 1.3:1 and less than about 1.7:1, most preferably from about 1.45:1 to about 1.55:1. It will be appreciated that in this embodiment of the process, the hydroxide excess (component III) is inherently fixed by use of calcium hydroxide as the source of both divalent metal and base. More generally it will be seen that the components II and III can separately be selected; for example, if calcium carbonate is used in a preneutralizing step (wherein calcium carbonate and said component I are mixed and carbon dioxide is evolved prior to sealing said reactor or prior to carrying out the malate-forming process of the invention) and the reaction mixture is then formed using calcium hydroxide, amounts of components II and III are independently controllable.

Particularly preferred component II/component I, (i.e., calcium/maleate) mole ratios being as specified above, preferred mole ratios of excess hydroxide/maleate (i.e. component III/I) herein are generally at least 0.2:1, more preferably from about 0.6:1 to about 1.4:1, most preferably from about 0.90:1 to about 1.1:1. as noted, there also exist preferred aqueous concentrations, or water contents, of the reaction mixture. In the malate-making process of the invention, the water content is generally in the range from about 10% to about 95 wt %, more preferably, about 40% to about 90%, most preferably, about 45% to about 73 wt % of the reaction mixture.

Very surprisingly, in the preferred range of calcium/maleate mole ratios (and especially in the most preferred range, about 1.45:1 to about 1.55:1), the reaction mixtures become more easily workable, forming an aqueous dispersion or suspension which comprises a unique, granular malate reaction product wherein the excess calcium hydroxide is intimately comixed, and wherein malate is formed in best yields. This product is unique and crystallographically distinct from common calcium malate, or calcium hydroxide, or simple mixtures of the two. Likewise, the product is crystallographically distinct from that prepared according to Example 1 of the above-cited Berg patent.

In its composition aspects, the invention encompasses these unusual malate-containing solid products, another very useful form of which can be obtained by using mixed calcium and magnesium cations at calcium:magnesium mole ratios in the above-summarized process of from about 0.99:0.01 to about 0.01:0.99, more preferably, from about 0.98:0.02 to about 0.80:0.20, most preferably, from about 0.97:0.03 to about 0.90:0.10.

The products of the malate-making process can directly be used for making malic acid. In another process also based on the invention, the products can be used for making 2,2'-oxodisuccinate laundry detergent builder salts (especially 2,2'-oxodisuccinic acid or sodium salt thereof). Thus, by using the above-described process step and treating the product thereof with mineral acid or any other convenient source of exchangeable $H^+$, malic acid is secured. By using the identical malate-making process and treating the product thereof with an additional amount of the component I (the reaction mixture now differing in composition in that both malate and maleate are essentially present) in the presence of solubilizing cation (such as sodium or potassium), 2,2'-oxodisuccinate is formed in high yield. It is a remarkable feature of the present invention that by conducting a two-step 2,2'-oxodisuccinate synthesis process, using the first step of forming malate salts in solid form near-quantitatively (at relatively high temperatures), and using another step of reacting the malate salts with additional maleate and solubilizing amounts of monovalent cation (at relatively lower temperatures), a more efficient conversion of component I to 2,2'-oxodisuccinate can be secured.

The invention has other preferred embodiments which are described in detail herein. Thus, in a typical commercial process for malate-making involving recycle steps, component I uses a mixture of maleate with one or more of 2,2'-oxodisuccinate, malate or fumarate. Indeed, it has been discovered that the malate-making process is generally capable of interconverting a mixture of these organic moieties to form malate in high yield. Component I will have a composition (weight %) in the following ranges for best results:

| Weight % | Generally Acceptable | Preferred | Most Preferred |
|---|---|---|---|
| maleate | 20–100 | 50–100 | 90–100 |
| malate | 0–50 | 0–30 | 0–10 |
| 2,2-'oxo-disuccinate | 0–50 | 0–30 | 0–10 |
| fumarate | 0–50 | 0–30 | 0–10 |

When component I has the above range of composition, the critical composition ratios illustrated in the simple embodiment above naturally require a more complex definition: the ratios will be calculated based on maleate feedstock taken as a whole, rather than on maleate alone. Making proper allowance for the total molar amount of carboxylate used as maleate, malate, 2,2'-oxodisuccinate and fumarate, the ratios in general are still in accordance with the simple illustration given above.

DETAILED DESCRIPTION OF THE INVENTION

General Considerations

The malate-making process of the instant invention is a high-yield process. Yields of 90 percent by weight or more are the norm. (Yields herein are based on weight percentage of the organic feedstock i.e., on the total weight of maleate+malate+2,2'-oxodisuccinate+fumarate used or present in the reaction mixture. See the analytical protocol hereinafter for further detail).

When not yield is the only consideration, yields of 99% or more can readily be achieved using the invention.

Maximizing yield of malate, however, is not the only consideration herein. The invention also provides selections of reaction conditions and compositions of the malate-making reaction mixtures especially suited for obtaining the malate-containing product herein as an unusual, easily handled granular solid. Thus, by selecting a reaction vessel having conventional means to drain spent liquors (e.g., by gravity), and by using specific, generally high, component II/I and component III/I mole ratios as further discussed hereinafter, the liquid phase of the reaction mixture may simply be drained at the end of the malate-making step, leaving the granular product in the reactor. This facilitates subsequent processes (e.g., malic acid or 2,2'-oxodisuccinate preparation) in the same reactor as is used for the malate synthesis.

Alternatively, separate reactors may be used for making each of the malate salts, malic acid and 2,2'-oxodisuccinate as provided for herein. For example, by modifying the reaction conditions and composition of the malate-making reaction mixture somewhat, a finer form of the above-mentioned solid granular malate-containing product is secured as a pumpable slurry, which can be readily transferred into the separate reactors used for converting the malate product of the invention to malic acid or 2,2'-oxodisuccinate. Such modification of the process uses the preferred temperatures and reaction times at the high end of the indicated ranges, or uses component I containing specific, limited amounts of fumarate, or uses component II containing specific, limited amounts of magnesium, to secure the desired slurries. These and other considerations are more fully described hereinafter.

A further aspect of the invention of considerable importance is that of the discovery of a process capable of controlling fumarate levels in product malate, or in product malic acid or 2,2'-oxodisuccinate derived therefrom.

Interconversion of Components

The results herein are especially surprising in view of the facts on one hand that Berg, despite use of varying reaction conditions, reports only mixtures of malate and 2,2'-oxodisuccinate. In our hands, the Berg process in fact also forms fumarate. The Berg process using calcium or magnesium is consistent with base-catalyzed Michael addition of maleate to in-situ formed malate, and fumarate is presumably derived, at least in part, from decomposition of 2,2'-oxodisuccinate. The present process for making malate avoids or minimizes such side-reactions, thereby selectively maximizing malate formation. On the other hand, current commercial processes for manufacture of malic acid, while operating at high (above reflux) temperatures similar to those herein, are also subject to fumarate-byproduct formation. Without being bound by theory, the instant process, through formation of an unusual, (typically alkaline, granular) solid form of malate as the divalent metal salt, may kinetically stabilize and protect the reaction mixture against the fumarate-forming tendency. It appears that a total of four organic species, i.e., maleate, malate, fumarate and 2,2'-oxodisuccinate, are involved in the instant reaction. Irrespective of the mechanisms involved, the present invention secures the means to control the interconversion of these species, thereby resulting in high yields of malate.

Reactor Design and Operating Pressures

The malate-making process of the invention has no pressure criticality. However, since it generally involves heating an aqueous mixture at temperatures above reflux, the malate-making reaction is usually carried out in a sealed reaction vessel of conventional construction, such as 316 SS (stainless steel). This reaction vessel need not be of titanium, nor need it be capable of withstanding high pressures, since the process (other than in handling of raw materials) is not corrosive and operates satisfactorily at low pressures. Pressures as low as about 30 psig (0.21 MPa) can be used; more typically, the process operates at pressures in the range up to about 150 psig (1.03 MPa). Most preferably, pressures from about 35 to about 85 psig (0.24 to about 0.59 MPa) are used. If desired, it is possible to operate at higher pressures but to no additional advantage. It is also possible to conduct the malate-making reaction in a reaction vessel which is not "sealed" in the conventional sense of the term: for example, evaporation of water is allowable provided that the reaction mixture does not boil dry at the reaction temperatures used. For this purpose, provision of a pressure head in the above-indicated range, or higher, maintained in the reaction vessel for the indicated reaction times, is sufficient. Thus, the reaction vessel may make use of pressurized, superheated steam introduced by means of direct injection, and may be equipped with steam outlets and/or pressure relief valves. Other aspects of reactor design e.g., stirring and heating means, are conventional.

Reaction Temperatures and Times

Reaction temperatures for the malate-making process herein are above reflux, generally at or above about 120° C. More preferably, temperatures in the range about 130° C. to about 220° C. are used. Most preferably, temperatures are in the range about 140° C. to about 190° C.

Reaction times for the malate-making process are of at least about 10 minutes, more preferably about 10 minutes to about 16 hours, most preferably about 30 minutes to about 6 hours. Reaction time is generally measured as of completion of loading of all the components of the malate-forming reaction mixtures into the reactor and bringing the mixture as rapidly as possible to the reaction temperature. Naturally, it will be appreciated that shorter reaction times are preferably accompanied by selection of higher reaction temperatures within the indicated ranges.

Components of Malate-forming Reaction Mixture

The components herein are component I, (having the above-tabulated composition), components II, (calcium, magnesium or mixtures of these divalent cations) and III excess base, (i.e., hydroxide ion); as noted, water is also present. As noted in a simple illustration of a preferred process according to the invention summarized above, component I may be in organic acid form and both components II and III together can conveniently be provided simultaneously, for example as calcium hydroxide. Alternatively, it is possible to adjust the amounts of each of components I, II and III independently.

In general, the malate-making process uses more than one mole of component II for each mole of maleate feedstock I. When the maleate feedstock comprises only dianions, e.g., when comprised of maleate and fumarate or maleate, fumarate and recycled malate, the preferred component II/I mole ratios are as given in the simple illustration of the process (using maleic anhydride and calcium hydroxide) hereinabove. When tetraanions i.e., 2,2'-oxodisuccinate, are also present in the maleate feedstock, the convention is used, for purposes of calculating reactant amounts, of expressing the total molar amount of component I on a divalent anion basis. In general, moles (I)=moles dianions in the sum of the moles of maleate+malate+2,2'-oxodisuccinate+fumarate charged in the malate-making reaction. Each mole of 2,2'-oxodisuccinate contributes 2 moles of dianion equivalents.

In the malate-making process herein, water is invariably present at least in an amount sufficient to allow reaction to occur (about 10 wt. %). In general, the malate-forming reaction mixture comprises about 10% to about 95%, more preferably about 40% to about 90%, most preferably about 45% to about 73% water. Also essential is that the reaction mixture should be alkaline i.e., in combining I, II and III in the presence of water, the reaction mixture should be neutralized and further, be rendered alkaline to the extent determined by amount of the excess base component, III. The moles of $H^+$ and $-OH$ involved in the neutralization of the reaction mixture (these amounts inherently resulting from the chemical form of the reactants) naturally form water, and are accounted for in defining the reaction mixture as aqueous. Further, in stating the water content of the reaction mixtures herein, water formed by neutralization is taken into account.

In general, the malate-making process herein uses a mole ratio of components III:I (i.e., excess base: organic component) of at least about 0.2:1. Preferably, this ratio is in the range from about 0.6:1 to about 1.4:1, most preferably from about 0.9:1 to about 1:1.

In general, the malate-making process herein uses a mole ratio of components II:I (i.e., divalent cation: organic component) of at least 1.1:1, more preferably greater than about 1.3:1 and less than or equal to about 1.7:1, most preferably, from about 1.45:1 to about 1.55:1.

The organic composition of the type I component being as noted, one satisfactory malate-making process according to the invention makes use of a type I component consisting essentially of from about 20% to about 100% maleate, from 0% to about 50% fumarate, from 0% to about 50% 2,2'-oxodisuccinate and from 0% to about 50% malate. More highly preferred is to use a high proportion of maleate, together with only limited amounts of one or more of the remaining three organic moieties malate, 2,2'-oxodisuccinate and fumarate. Thus, as noted, a more preferred feedstock I comprises about 50-100%, (most preferably about 90-100%) maleate, the balance of I being malate, 2,2'-oxodisuccinate, fumarate or mixtures thereof. Typically, most highly preferred commercial processes based on the invention accommodate recycled (or initially charged) malate, 2,2'-oxodisuccinate or fumarate amounts each in the range of from 0% to about 10% by weight of the total of component I.

The malate-making process of this invention is effective where magnesium alone is used as component II. However, if a single divalent cation is used, calcium should be used as component II to secure the highest yield. Remarkably, if component II consists essentially of mixtures of calcium with relatively small proportions of magnesium, malate yields of greater than 99% are secured. When using calcium/magnesium mixtures as component II herein, the calcium/magnesium mole ratios are typically from about 0.99:0.01 to about 0.01:0.99, more preferably, from about 0.98:0.02 to about 0.80:0.20, most preferably, from about 0.97:0.03 to about 0.90:0.10.

Generally, the malate-making process of the invention is operated using aqueous alkaline reaction mixtures consisting essentially of components I, II, II and water. However, other cations, such as monovalent metal cations may additionally be present. When component II consists essentially of calcium, it has been discovered that the total amount of additional, soluble monovalent cations, should be controlled at or below about 0.4 mole fraction of the total of non-hydrogen cations in order to achieve optimum yields. In general, expressing the total amount of non-hydrogen (monovalent and polyvalent) cations in the malate-forming reaction mixture as 1 mole (1.0 mole fraction), one preferred process of the invention uses a total non-hydrogen cation composition comprising or consisting of from about 0.8 to about 1.0 (more preferably about 0.9 to about 1.0, most preferably about 1.0) mole fraction calcium, magnesium or mixture thereof. Optionally, in this preferred process, sodium, potassium, mixture of said sodium and potassium, or equivalent solubilizing monovalent cation e.g., tetraalkylammonium or the like, can be present at levels of from 0 to about 0.2, e.g., about 0.1 mole fraction of the total of non-hydrogen cations.

Chemical and Physical Forms of Reactants

In general, the malate-producing and subsequent malic acid or 2,2'-oxodisuccinate-making process steps herein are not particularly limited with respect to the chemical or physical form of the reactants, provided that reaction mixtures having the specified proportions of the essential components are used. An extensive list of useful reactants can be drawn up; this list includes any of the maleates, malates, 2,2'-oxodisuccinates, fumarates, oxides, hydroxides, carbonates and bicarbonates of calcium or magnesium. Likewise included are maleic anhydride (preferred), maleic acid, fumaric acid and 2,2'-oxodisuccinic acid as well as any mixed or partial salt of the foregoing cations and anions.

As noted, sodium, potassium and similar solubilizing monovalent cations in water-soluble salt form are optionally used and are only tolerated in the malate-making process at limited levels, contrasting with the 2,2'-oxodisuccinate-making process discussed hereinafter wherein the solubilizing effect of such cations is essential. Since the chemical forms of such monovalent cations include tetrasodium 2,2'-oxodisuccinate and mixed sodium/calcium 2,2'-oxodisuccinates, recycle of such sodium/calcium-2,2'-oxodisuccinates from a 2,2'-oxodisuccinate making step (described hereinafter) into the malate-making step should preferably be limited in accordance with the above-noted limitations on composition of component II and on overall nonhydrogen monovalent cation content of the malate-making reaction mixtures.

In general, the chemical form of the non-hydrogen cations herein will be that of oxide, hydroxide such as calcium hydroxide, magnesium hydroxide or the like, or inert anion salts. For purposes of preneutralizing component I, salts such as calcium carbonate may be used. Inert anions, e.g., sulfate, can optionally be present herein; but most preferably, inert anions are not used. Process aids e.g., silicates, aluminates, surfactants and hydrotropes can optionally be used in the processes of the invention. Low levels of fumarate or magnesium are desirable in the starting compositions of the malate-making process herein (preferred malate, malic acid or 2,2'-oxodisuccinate product compositions however typically have fumarate levels below about 7% by weight of the organic moieties).

Embodiments of the Invention Maximizing Yields of Malate

Maximum yields of malate in the malate-forming process of the invention are readily obtainable by simply selecting temperatures, times, proportions and chemical forms of components I, II, III, and amounts of water, each as indicated hereinabove.

It will be appreciated that for best results, the above-mentioned parameters will not be selected independently from one another. Thus, use of the lowest reaction temperatures is generally accompanied by selection of longer reaction times, and vice-versa. See, for example, Table 1 and the tabulated results in Examples II–XV hereinafter: in Example II, a yield of 88.8% is obtained by selecting a reaction temperature of about 120° C. and the rather long reaction time of 16 hours. In contrast, and more preferably, at the higher temperature (about 165° C.) of Example XIV, a yield of 94.9% is obtained after only one hour.

Table 1 provides detailed non-limiting illustrations of conditions under which best possible yields of malate may be obtained. (See the Examples, especially Examples I, XV, and XX hereinafter, for additional procedural details).

TABLE I

| Embodiment No. | Component I Moles (Wt. %) | Component II Moles ($Ca^{2+}$) | | Component III (−OH excess, Moles) | Water Content Wt. % | Moles II/I | Moles III/I | Composition Component II Ca:Mg Mole Ratio | Chemical Form of Reactants/ Order Charged | Reaction Temperature °C. |
|---|---|---|---|---|---|---|---|---|---|---|
| 1 | maleate 1 (100%) | $Ca^{2+}$ $Mg^{2+}$ | 1.33 0.17 | 1.0 | 70.6 | 1.5:1 | 1:1 | 0.89:0.11 | Footnote 1 | 180 |
| 2 | maleate 1 (100%) | $Ca^{2+}$ $Mg^{2+}$ | 1.45 0.05 | 1.0 | 70.3 | 1.5:1 | 1:1 | 0.97:0.03 | Footnote 2 | 145 |
| 3 | maleate 1 (100%) | $Ca^{2+}$ $Mg^{2+}$ | 1.45 0.05 | 1.0 | 70.3 | 1.5:1 | 1:1 | 0.97:0.03 | Footnote 3 | 165 |
| 4 | maleate 1 (100%) | $Ca^{2+}$ $Mg^{2+}$ | 1.455 0.045 | 1.0 | 70.3 | 1.5:1 | 1:1 | 0.97:0.03 | Footnote 4 | 148 |
| 5 | maleate 1 (100%) | $Ca^{2+}$ $Mg^{2+}$ | 1.40 0.00 | 0.8 | 71.3 | 1.4:1 | 0.8:1 | 1.00:0 | Footnote 5 | 165 |
| 6 | maleate 1 (100%) | $Ca^{2+}$ $Mg^{2+}$ | 1.5 0.00 | 1.0 | 70.2 | 1.5:1 | 1:1 | 1.00:0 | Footnote 6 | 180 |
| 7 | maleate 1 (91%) malate 0.1 (9%) | $Ca^{2+}$ $Mg^{2+}$ | 1.50 0.00 | 0.9 | 68.9 | 1.5:1 | 0.9:1 | 1.00:0 | Footnote 7 | 165 |
| 8 | maleate 1 (100%) | $Ca^{2+}$ $Mg^{2+}$ | 1.20 0.00 | 0.4 | 52.7 | 1.2:1 | 0.4:1 | 1.00:0 | Footnote 8 | 180 |
| 9 | maleate 1 (100%) | $Ca^{2+}$ $Mg^{2+}$ | 1.30 0.00 | 0.6 | 72.4 | 1.3:1 | 0.6:1 | 1.00:0 | Footnote 9 | 145 |

| Embodiment No. | Reaction Time Hrs. | Wt. % (HPLC) | | | | Product Character |
|---|---|---|---|---|---|---|
| | | Malate | 2,2′-oxo-disuccinate | Fumarate | Maleate | |
| 1 | 6 | 98.0 | 1.3 | 0.5 | 0.2 | Pumpable slurry of granular malate |
| 2 | 6 | 98.9 | 0.3 | 0.8 | 0 | Pumpable slurry of granular malate |
| 3 | 6 | 99.2 | 0.2 | 0.6 | 0 | Pumpable slurry of granular malate (See Example XX) |
| 4 | 7 | 98.8 | 0.3 | 0.9 | 0 | Pumpable slurry of granular malate |
| 5 | 6 | 98.1 | 0.7 | 1.1 | 0 | Pumpable slurry of granular malate |
| 6 | 2 | 96.0 | 2.4 | 1.6 | 0 | Coarse granules readily separable by decantation or filtration from the aqueous liquor (See Examples XV, XVI) |
| 7 | 7 | 99.2 | 0.2 | 0.6 | 0 | Coarse granules |
| 8 | 6 | 95.8 | 1.8 | 2.4 | 0 | Hard solid mass |
| 9 | 6 | 95.0 | 2.1 | 2.9 | 0 | Hard solid mass |

[1] 1 mole maleic anhydride; 433.7 g water*; 0.17 mole magnesium hydroxide and 1.33 moles calcium hydroxide.
[2] 1 mole maleic anhydride 431.7 g water*; 0.05 mole magnesium hydroxide and 1.45 moles calcium hydroxide.
[3] 1 mole maleic anhydride 431.7 g water*; 0.05 mole magnesium hydroxide and 1.45 moles calcium hydroxide.
[4] 1 mole maleic anhydride 431.7 g water*; 0.045 mole magnesium hydroxide and 1.055 moles calcium hydroxide.
[5] 1 mole maleic anhydride 438.3 g water*; 1.4 moles calcium hydroxide.
[6] 1 mole maleic anhydride 431.0 g water*; 1.5 moles calcium hydroxide.
[7] 1 mole maleic anhydride 441.0 g water*; 1.4 moles calcium hydroxide; 0.1 mole calcium malate.
[8] 1 mole maleic anhydride 180.0 g water*; 1.2 moles calcium hydroxide.
[9] 1 mole maleic anhydride 463.7 g water*; 1.3 moles calcium hydroxide.
*Total water including that liberated in neutralization.

As noted hereinabove, absolute maximization of yield is not the only consideration herein, and Table 1 also illustrates especially preferred embodiments of the invention where it is desired to isolate the granular solid product (e.g., by filtration; see embodiment 6 in the Table) or where it is desired to obtain a readily pumpable slurry of the same granular form of malate (having a lower mean particle size; see embodiments 1–5).

Table 1 also illustrates high-yield malate synthesis where the reaction mixture forms a less desirable hard mass (see embodiments 8 and 9), which lacks the attractiveness of handling displayed by the coarse or fine (pumpable) granular forms. The latter, more desirable forms of the product arise at component II/I mole ratios within the preferred (>1.3:1 and ≦1.7:1) ranges, especially good results being obtained at II/I mole ratios of 1.4:1 or 1.5:1. In contrast, using a II/I mole ratio of 1.3:1 or less (see embodiments 8 and 9), the less desirable hard mass of malate product is obtained. For purposes of comparison, these less desirable II/I mole ratios correspond with those used by Berg and Lamberti et al., cited hereinabove.

In connection with the preferred embodiments of the invention, it is also generally advantageous to use relatively high masses of reactants in relation to amounts of water. Note that the terms "aqueous concentration" and "pH" are generally avoided herein, in view of the fact that the malate-forming process step is a two-phase reaction, so that pH does not accurately reflect the amount of hydroxide excess in the reaction mixture. The term "aqueous concentration" is likewise unuseful, in view of the generally high proportions of reactant species which are not in solution at any given point in time.

Also, in connection with Table 1, it is noteworthy that the combined advantages of high yield, high purity of the organic component of the product, and readily pumpable product all occur simultaneously at the illustrated calcium: magnesium molar proportions (see embodiments 1–4). Likewise beneficial to improve formation of a fine, pumpable granular product are any of: high reaction temperatures, longer reaction times, or presence of limited amounts of malate or fumarate in component I (see also for example embodiment 7, the product of which is also granular, or Examples XXIII or XXVI hereinafter).

Preferred Embodiments of the malate-making process involving particular selections of reactant forms or involving recycle The malate-making process herein may make use of particular selections of reactant forms, or may involve recycle, depending upon economical sources or recycle streams available to the manufacturing facility. Most simply as illustrated hereinabove, maleic anhydride and calcium hydroxide will suffice.

However, the invention also encompasses a malate-making process using recycle of a portion of said component I; in a simple illustration, fresh maleate (0.8 mole fraction) and recycled fumarate (0.2 mole fraction) is charged in the malate-making reactor together with the components II, III and water as specified above. In more complex illustration using a pre-neutralization step involving calcium carbonate (which may optionally be a recycled calcium carbonate stream), the invention encompasses an aqueous alkaline process for securing malate in a solid, alkaline, calcium or mixed calcium/magnesium salt form by the steps comprising, in sequence:

1. reacting maleic anhydride or maleic acid and calcium carbonate to form a mixture;
2. permitting carbon dioxide to evolve;
3. rendering said mixture alkaline using calcium hydroxide or mixture thereof with magnesium hydroxide; all provided that said reactants are used at a (calcium+magnesium): maleate molar ratio in the range from greater than about 1.3:1 to less than (or equal to) about 1.7:1, a calcium:magnesium mole ratio in the range from about 1.00:0.00 to about 0.80:0.20, a water content in the range from about 45% to about 73% and an excess of hydroxide of from about 0.6 to about 1.4 moles per mole of maleate used; and
4. reacting said mixture in a sealed vessel at temperatures in the range from about 140° C. to about 190° C. for a period of from about 0.5 to about 6 hours.

In this illustration, it is readily possible to use a fumarate-containing maleate reactant in said step 1 to the extent of not more than about 0.2 moles of fumarate being present per mole of said maleic anhydride or maleic acid added in each cycle.

Another embodiment of the invention, highly preferred when the malate-making step is coupled with a subsequent 2,2'-oxodisuccinate-forming step (see the disclosures hereinafter), uses the following reactants to charge the malate-making reactor: water, calcium carbonate filter cake from the 2,2'-oxodisuccinate process, (said filter cake containing limited amounts of sodium 2,2'-oxodisuccinate salts) and maleic anhydride. These reactants are charged in any order, and carbon dioxide evolution is allowed to reach completion. Finally, excess hydroxide (component III) and the balance of the necessary calcium are added simultaneously as calcium hydroxide. The malate-forming reaction is then carried out in the usual manner. In this embodiment, calcium may optionally be recycled by use of a lime kiln to convert calcium carbonate byproduct of the 2,2'-oxodisuccinate process into calcium hydroxide. Likewise optionally present by way of additional recycle streams may be limited amounts any one or more of fumarate, malate or 2,2'-oxodisuccinate, within the ranges indicated hereinabove.

Novel Malic Acid Process

As noted, by simply acidifying the divalent cation-containing product of the malate-making step herein, the divalent cation may be displaced, so that malic acid is obtained. Thus, the invention encompasses a process for the manufacture of malic acid using the above-defined malate-making process, followed by an acidification step. In view of the high purity of the organic component produced in the malate-making process herein, as well as of economic considerations, a malic acid process using the present invention offers considerable advantages. For example, a typical malate-containing product with very low levels of fumarate requires little organic purification.

Novel Compositions

In its composition aspects, the present invention encompasses the unusual granular, solid products of the malate-making process, the most preferred forms of which are the relatively coarse, easily filterable granule and finer pumpable (in water or mother liquor of the reaction) granule described above. As noted, the processing advantages of these forms of malate are considerable, especially in that they are very readily separated from the aqueous phase of the reaction mixture on one hand, while not forming intractable, large solid masses on the other.

As will be seen from the Examples hereinafter, experimental evidence confirms that such granular forms of malate are of unique crystallographic composition, as confirmed by X-ray analysis.

Illustrative of typical organic compositions of the preferred malate product are embodiments 1–7 shown in Table 1. In general, such granular product of the preferred malate-making processes comprises on a dry weight basis, based on malate and maleate and 2,2'-oxodisuccinate and fumarate, from about 70% to about 99.5% (more preferably from about 90% to about 99.5%) malate. On the same basis, the organic balance of the composition typically comprises from 0% to about 30% (more preferably less than about 3%) fumarate, from 0% to about 30% (more preferably less than about 3%) 2,2'-oxodisuccinate and from 0% to about 30% (more preferably less than about 2%) maleate. The inorganic composition is simply determined on the basis of the amounts of calcium and/or magnesium, and hydroxide excess used. A preferred malate product is further characterized in that it is directly obtainable by said process in alkaline, preferably granular, solid form as noted, further characterized in that it contains a form of calcium malate. Based upon the unique X-ray crystallographic characterization of such product, the invention encompasses a novel composition of matter comprising malate and calcium, said composition comprising a major crystalline component having a characteristic d-spacing of 8.597 Å ($2\theta = 10.28°$) as measured using Cu $K_\alpha$ radiation (see the experimental disclosure hereinafter for further details). To be noted is that said alkali, i.e., hydroxide, and calcium cannot be simply removed from the composition without destroying the unique crystalline form thereof; also noteworthy is that d-spacings characteristic of calcium hydroxide are absent or present only at low levels in the crystallographic data. Also encompassed herein is the analogously prepared mixed calcium/magnesium and magnesium forms of such composition.

Novel 2,2'-oxodisuccinate Process

In addition to the novel malate-making and malic acid process, the present invention also provides a preferred starting material for an improved alkaline process for forming 2,2'-oxodisuccinate. Thus, if the above-described malate-making process is identified as step (a), the invention also encompasses a process for the manufacture of 2,2'-oxodisuccinate as the acid or any sodium salt, e.g., tetrasodium 2,2'-oxodisuccinate, characterized in that said process comprises at least one malate-making step (a) as defined hereinabove, followed by at least one step (b) of reacting the malate-containing product thereof with freshly added maleate.

In the above, a preferred step (b) involves reacting the malate-containing product of step (a) together with maleate and solubilizing monovalent cations selected from sodium, potassium and mixtures thereof in aqueous alkaline media, typically at or below reflux temperatures, preferably at temperatures in the range from about 65° C. to about 85° C., preferred reaction times being in the range from about 1 to about 6 hours, to provide 2,2'-oxodisuccinate.

A highly preferred process herein also has an additional step, (c), which comprises maintaining the mixture formed in step (b) at a temperature lower than the step (b) reaction temperature. Preferably, the lower temperature is in the range from about 20° C. to about 60° C. and this temperature is maintained for a period of from about 6 hours to about 21 days. Optionally, a step (d) of conventionally converting the 2,2'-oxodisuccinate-containing product of steps (b) or (c) to acid or sodium salt form may also be used.

In detail, step (b) in any such process involves forming, in the presence of a solubilizing monovalent cation component, a reaction mixture comprising the components maleate, malate, water, hydroxide excess and a divalent cation selected from calcium, magnesium and mixtures thereof, with the proviso that the product of the malate-making process herein is used as malate source. (Thus, with the exception of the solubilizing cation component and the requirement of both maleate and malate, the essential components used closely resemble the essential components of the malate-making step as defined hereinabove).

Such 2,2'-oxodisuccinate forming process differs from art-known processes for preparing 2,2'-oxodisuccinate in several important respects. Compared with the above-cited procedures of Berg, U.S. Pat. No. 3,128,287, and Niewenhuizen et al., J. Amer. Chemists' Soc., Vol. 60, 1983, pages 44-48, incorporated herein by reference, the instant process differs in that it requires the use of the above-mentioned solubilizing monovalent cation component. Any such component, such as water soluble forms of the cations, sodium, potassium or tetramethylammonium, will suffice. Sodium, potassium and mixtures thereof are preferred; sodium is especially preferred.

Remarkably, in view of the simplicity of such a process, very significant advantages are obtained over the use of any art-disclosed processes for making 2,2'-oxodisuccinate. The process, for example, secures any of: shortened reaction times (for given yields of 2,2'-oxodisuccinate as compared with art-known processes), improved yields of 2,2'-oxodisuccinate, and unique and useful product compositions. In the preferred embodiment, all of these advantages are obtainable concurrently. Notable among several additional advantages of the process, it is workable, indeed preferably operated, at lower water content than made possible using art-taught processes. The practitioner may apply this advantage to achieve higher and more economical throughput for a given investment in process equipment to form 2,2'-oxodisuccinate. Also, the process yields less fumarate for each mole of 2,2'-oxodisuccinate formed. (Fumarate byproduct lacks the effectiveness of ODS as a detergent builder.)

As noted, the essential components used in forming 2,2'-oxodisuccinate-producing reaction mixtures herein use generally similar chemical and physical forms to those used in the malate-making step. Some significant differences do, however exist: i.e., in the selection of essential reactants as noted; in their proportions; and in the reaction conditions.

Thus, an organic component (analogous to component I is in the malate-making step) is used but this now has an initial maleate/malate mole ratio preferably in the range from about 0.9:1 to about 2:1; more preferably about 1:1 to about 1.6:1; most preferably about 1.2:1 to about 1.5:1. Divalent cation component (analogous to component II in the malate-making step) is also used but this now has a mole ratio calcium: (maleate+malate) from about 0.1:1 to about 1.05:1, more preferably about 0.19:1 to about 0.90:1, most preferably from about 0.41:1 to about 0.77:1. Magnesium may also be present in this component, but when magnesium is used, it preferably substitutes only a limited proportion of the calcium in the above-defined mole ratios. Calcium: magnesium mole ratios in general in step (b) are from about 1:0 to about 0:1, more preferably about 0.80:20 to about 1.00:0.00, most preferably about 0.97:0.03 to about 1.00:0.00.

In the 2,2'-oxodisuccinate-making step (b), hydroxide excess, defined similarly to component III in the malate-making step (a), is present at levels in the 2,2'-oxodisuccinate-making step (b)) in the range from about 0.001 to about 1 mole, more preferably from about 0.01 to about 0.4 moles, most preferably about 0.02 to about 0.15 moles, per mole of component I (i.e., most simply, per mole of maleate+malate).

Solubilizing monovalent cation $M^+$, essential in the 2,2'-oxodisuccinate-making step as noted, is most preferably sodium. Such cation is used at a $M^+$/(maleate+malate) mole ratio in the range from about 0.66:1 to about 2.12:1; more preferably about 0.66:1 to about 1.62:1; most preferably about 0.66:1 to about 1.28:1.

Water content of the 2,2'-oxodisuccinate-forming reaction mixture of step (b) is from about 25% to about 80%, more preferably about 35% to about 60%, most preferably from about 38% to about 50%. In practice, a particular amount of the product of the malate-making process is selected, and based upon its composition, appropriate amounts of the remaining reactants for the 2,2'-oxodisuccinate-making step are selected.

Generally, component I in the 2,2'-oxodisuccinate making step may optionally contain 2,2'-oxodisuccinate or fumarate (e.g., recycled or present by virtue of presence in the product of the malate-making step). In general, component I may be recycled in the process. The above-defined mixture is typically reacted at a temperature ("step (b) reaction temperature") in the range from about 60° C. to about 120° C., more preferably about 65° C. to about 85° C., most preferably about 70° C. to about 83° C. for periods ("step (b) reaction time") of from about 0.2 to about 24 hours, more preferably about 0.5 to about 12 hours, most preferably about 1 to about 6 hours to produce a mixture, comprising 2,2'-oxodisuccinate in high (typically above about 70%) yield.

During the 2,2'-oxodisuccinate-forming step (b) of the invention, the above-defined reaction mixture forms a homogeneous pumpable fluid, which can at any subsequent time be cooled to ambient temperature, and be kept or used whenever desired as a source of 2,2'-oxodisuccinate, for example, by conventionally exchanging calcium for sodium and using the sodium form as a detergent builder. To ensure that it is quite clear what is meant by "homogeneous pumpable fluid", see the following typical data, which illustrate conditions under which said fluid is pumpable (typically, relative viscosity is less than about 3000 centipoise).

| Water Content (by Weight) | Temperature of Measurement | Component II/I mole ratio; e.g. Ca/maleate + malate) used in the reaction |
| --- | --- | --- |
| 38% or higher | 35° C. or higher | about 1.3:1 |
| 38% or higher | 45° C. or higher | about 1.4:1 |
| 38% or higher | 65° C. or higher | about 1.6:1 |

Clearly, some conditions exist when the fluid product of the invention is not pumpable, for example when in frozen or dried solid form. The formation of the pumpable fluid is especially useful at high solids content (i.e., low water levels). The data also illustrate a strong dependence of viscosity upon component II/I mole ratios.

"Homogeneous" herein is more readily understood upon recognizing that typically, the "homogeneous pumpable fluid" has the visual appearance of honey containing a little beeswax. Thus, although it may contain undissolved solids, it is very different from the reaction mixtures formed using art-disclosed 2,2'-oxodisuccinate synthesis methods in that it is neither chalky in appearance, nor is it watery or easily separable into solid and liquid phases. Optical microscopy further confirms that high proportions of a continuous phase and low amounts of solid are present. When carrying out the preferred process of the invention as disclosed herein, the homogeneous pumpable fluid can be made which to the eye appears as a clear, single, liquid phase. Formation of such a phase (or indeed the more generally observed homogeneous pumpable fluid) at the very high dissolved solids content disclosed herein, despite the presence of large amounts of calcium salts known to be rather insoluble, is a remarkable and useful aspect of the present invention.

The crude 2,2'-oxodisuccinate-containing product (i.e. the above-defined fluid reaction mixture) herein is also usefully characterized in that, by weight of the organic moieties 2,2'-oxodisuccinate+maleate+malate+fumarate in total, it comprises from about 50% to about 85% or even higher levels of 2,2'-oxodisuccinate. Typically, about 70% to about 85% of said organic moieties are 2,2'-oxodisuccinate. On a similar basis, typical fumarate levels are less than about 25%; e.g. about 3% to about 15%, or, more preferably about 0.2% to about 10%. The balance of the organic moieties comprise or consist of maleate, malate, or mixtures thereof. In general, it should be appreciated that for any given reaction, higher yields of 2,2'-oxodisuccinate are usually accompanied by some increase in fumarate levels, albeit that it is minimized by the process herein.

It should be appreciated that the 2,2'-oxodisuccinate-forming process of the invention has a maximum yield of 2,2'-oxodisuccinate significantly higher than that disclosed in the art when the divalent metals, calcium or magnesium are used. Furthermore, achieving the control of fumarate levels herein is a major advantage of the invention.

The balance of the crude 2,2'-oxodisuccinate product composition, prior to any drying or workup, will generally be made up largely, if not exclusively, of water, hydroxide anions and the nonhydrogen cations initially used. (Note that in solid form, it is not intended to suggest that these ions are dissociated).

As for the precise methodology used in the above-defined 2,2'-oxodisuccinate making step, it is noted that the product of the malate-making step together with the components required to produce the above-defined 2,2'-oxodisuccinate-forming mixtures are typically contacted at mixing temperature below about 120° C., more preferably about 20° C. to about 120° C., most preferably about 60° C. to about reflux temperature; the objective being, especially when particular chemical forms of the components, such as maleic anhydride are available, to use the heat obtainable by exothermic hydration and neutralization reactions, which are rapid, without allowing any extended period of maintaining the reaction mixture at high temperature. During contacting of the components, the formation of "hot spots" in the mixture is generally avoided by use of means for cooling, stirring or other conventional means well known in the art. After contacting the components, the reaction mixture is reacted at a step (b) reaction temperature in the hereinabove-noted range. Most preferably, after the contacting operation, the reaction mixture is brought within this range of temperature as rapidly as possible. The reaction mixture is then maintained at the reaction temperature for the hereinabove-noted step (b) reaction time. The reaction mixture contains useful levels of 2,2'-oxodisuccinate after periods as short as a few minutes or, in any event, as soon as the above-described homogeneous pumpable fluid is formed.

An important aspect of the invention is that, after forming the above-defined homogeneous pumpable fluid, it is immediately possible to lower the reaction temperature and thereby to limit fumarate formation. In order to achieve the highest possible yields of 2,2'-oxodisuccinate at acceptable fumarate levels and within short periods of time, the following method is adopted: the 2,2'-oxodisuccinate-forming step (b) described above is followed, after a reaction time of about 1 to about 6 hours at a reaction temperature of about 70° C. to about 83° C. by a "maturation" step (step (c) hereinafter) wherein the 2,2'-oxodisuccinate containing reaction mixtures are simply cooled to a temperature ("maturation temperature") in the range from about ambient (e.g., 20° C.) to about 60° C., at which the mixtures are simply stored for a period of from about 8 hours to about 21 days. ("Maturation Time") This procedure results in typical organic composition of from about 80% to about 95% of 2,2'-oxodisuccinate, with low levels (e.g., about 0.2-10%) fumarate, the organic balance comprising maleate, malate or mixtures thereof. Since the malate-making step herein is near quantitative, the combination of malate-making (a), 2,2'-oxodisuccinate-making (b) and maturation (c) steps result in high overall conversions of maleic anhydride or maleic acid to 2,2'-oxodisuccinate.

After the three reaction steps in the 2,2'-oxodisuccinate synthesis have been completed, the divalent metal content of the aqueous reaction mixture may be reduced by conventional means. For example, removal of divalent metal can be carried out in a number of ways known in the art, such as by simply adding a precipitating material. Such calcium or magnesium precipitating materials include alkali metal carbonate and/or bicarbonate (preferred), ethane hydroxydiphosphonate, pyrophosphate and/or alkali metal silicate. The resulting calcium precipitate can thereafter be removed from the aqueous reaction product mixture by filtration and as noted hereinabove, may optionally be recycled, for example in carbonate salt form. In an alternative procedure, removing calcium from the aqueous 2,2'-oxodisuccinate reaction product mixture involves treatment of said mixture with an appropriate insoluble ion exchange resin. No matter what technique is employed, divalent metal content of 2,2'-oxodisuccinate salts prepared by methods herein should desirably be reduced to the extent that calcium comprises from about 0.2% to about 1.0% of the 2,2'-oxodisuccinate salt in order to form compositions preferred as detergent builders. The calcium-replacing cation is typically H+ or Na+, most usually Na+. When magnesium 2,2'-oxodisuccinates are also present in the crude product, it is less critical, and may even be undesirable to replace all magnesium with H+ or Na+ if the 2,2'-oxodisuccinate product is to be used as a laundry detergent builder; however treatment with alkali metal carbonate etc., as noted hereinabove, will generally deplete levels of both calcium and magnesium in the 2,2'-oxodisuccinate salts to any level desired by the formulator.

All ratios and proportions herein are on a mole basis, and percentages are by weight unless otherwise indicated. Mole ratios are based on the amounts of components prior to carrying out the processes of the invention unless otherwise noted. Yields are expressed as percentages by weight of the total of the organic species maleate, malate, 2,2'-oxodisuccinate and fumarate, as determined by HPLC chromatography.

EXAMPLES ILLUSTRATING NOVEL SOLID-FORM MALATE AS CALCIUM OR MAGNESIUM SALTS

EXAMPLE 1

Maleic anhydride (29.4 g, 0.3 moles, Aldrich) is dissolved in distilled water by heating to about 85°-90° C. in an open preweighted Hastalloy C autoclave (Parr Instrument Co., Model 4561, 300 cc) and stirring. The solution is cooled by placing the autoclave in an ice-bath. When a temperature of 60°-80° C. is reached, calcium hydroxide (33.3 g, 0.45 moles, Aldrich, A. C. S.) addition is started. A thick paste forms, which thins significantly as addition of calcium hydroxide progresses. When all the calcium hydroxide is added, the total reaction weight is corrected by adding water to a reaction mixture weight of 192.0 g. The water content is calculated as 70.2%. The autoclave is sealed, placed in a 165° C. thermostat-equipped oil bath and stirred. After bringing the reaction mixture to equilibrium with the oil bath temperature, further stirring is continued for 4.5 hours (the reaction time as defined herein). Note that the oil bath and autoclave are previously calibrated: it is shown that an oil bath temperature of about 165° C. corresponds with an internal autoclave temperature of about 145° C. Pressure reaches a maximum of 45 psig (0.31 MPa; where 1 psi=0.006895 MPa). The autoclave is cooled in water, opened, and weighed. The weight is within 2 g; insignificant leakage of the autoclave is thereby demonstrated. The contents of the autoclave are comprised primarily of a granular product, white in color and odorless. No off-odors are detected. (When very high temperatures, 185° C. or more, are used, the product acquires trace odor and trace impurity peaks in HPLC analysis.) The autoclave also contains some finer solids and a thin crust on the internal walls. All contents are readily scraped out and rinsed into a WARING BLENDOR. Using distilled water, the sample weight is made up to 320 g and blended for the purpose of homogeneous sampling for analysis. (For workup, simply acidify with sulfuric acid and separate calcium sulfate leaving a solution of malic acid or, simply filter and air dry; or, use for making 2,2'-oxodisuccinate, as desired.) 0.4 g samples of the Waring-blended product mixture are quenched in 100 cc lots of 0.1N $H_2SO_4$ with vigorous shaking, and the samples are submitted for HPLC analysis. Analysis indicates that by weight % of organic components, the product comprises 94.7% malate. 2.1% 2,2'-oxodisuccinate and 3.2% fumarate are copresent. No maleate is detected.

EXAMPLES II-XV

Using the procedure of Example I, together with preferred calcium/maleate mole ratios in the range 1.4:1-1.5:1 moles/mole, temperature, pressure and time vs organic composition of the reaction mixture are studied. Results are tabulated below in Table 2.

TABLE 2

| Example No. | Calcium/ Maleate Mole Ratio | Maximum Pressure (psig) Observed | Oil Bath t °C. | Reaction Mixture t °C. | Time Hours | Weight % (HPLC) Malate | Weight % (HPLC) ODS* | Weight % (HPLC) Fumarate | Weight % (HPLC) Maleate |
|---|---|---|---|---|---|---|---|---|---|
| II | 1.5:1 | not measured | 135 | 120 | 16 | 88.8 | 8.2 | 3.0 | 0 |
| III | 1.5:1 | 35 (0.24 MPa) | 145 | 130 | 8 | 92.9 | 2.5 | 4.6 | 0 |

TABLE 2-continued

| Example No. | Calcium/ Maleate Mole Ratio | Maximum Pressure (psig) Observed | Oil Bath t °C. | Reaction Mixture t °C. | Time Hours | Weight % (HPLC) Malate | Weight % (HPLC) ODS* | Weight % (HPLC) Fumarate | Weight % (HPLC) Maleate |
| --- | --- | --- | --- | --- | --- | --- | --- | --- | --- |
| IV | 1.5:1 | not measured | 155 | 140 | 4 | 94.4 | 2.1 | 3.4 | 0.1 |
| V | 1.5:1 | not measured | 155 | 140 | 10 | 95.7 | 1.4 | 2.9 | 0 |
| VI | 1.5:1 | not measured | 155 | 140 | 1 | 30.6 | 12.9 | 7.8 | 48.7 |
| VII | 1.5:1 | not measured | 155 | 140 | 2.4 | 70.6 | 14.3 | 10.6 | 4.5 |
| VIII | 1.5:1 | 40 (0.28 MPa) | 155 | 140 | 4 | 94.1 | 3.5 | 2.4 | 0 |
| IX | 1.5:1 | 42 (0.29 MPa) | 155 | 140 | 4 | 94.2 | 2.9 | 2.9 | 0 |
| X | 1.5:1 | 35 (0.24 MPa) | 155 | 140 | 4 | 93.3 | 3.2 | 3.5 | 0 |
| I | 1.5:1 | 45 (0.31 MPa) | 165 | 145 | 4.5 | 94.7 | 2.1 | 3.2 | 0 |
| XI | 1.5:1 | 42 (0.29 MPa) | 165 | 145 | 4.25 | 93.5 | 2.7 | 3.9 | 0 |
| XII | 1.4:1 | 56 (0.39 MPa) | 165 | 145 | 6 | 97.8 | 0.4 | 1.8 | 0 |
| XIII | 1.4:1 | 80 (0.55 MPa) | 165 | 145 | 6 | 98.1 | 0.7 | 1.1 | 0 |
| XIV | 1.5:1 | 115 (0.79 MPa) | 185 | 165 | 1 | 94.9 | 2.5 | 2.6 | 0 |
| XV | 1.5:1 | 120 (0.83 MPa) | 200 | 180 | 2 | 96.0 | 2.4 | 1.6 | 0 |

(All of Examples I–XV use 70–72% weight % water)
*ODS = 2,2'-oxodisuccinate

Example II confirms that even at relatively low temperatures in the preferred range, results quite different from those of Berg are obtained: only 8.2% 2,2'-oxodisuccinate is present. Examples VI, VII and VIII are particularly instructive in that they demonstrate that mixtures having appreciable proportions of 2,2'-oxodisuccinate, maleate and fumarate can be converted to malate in high yield. The remaining Examples generally illustrate high yields with low residual levels of fumarate, and the varying times, temperatures and pressures herein.

EXAMPLE XVI

Air-dried samples of the solid product of Example XV are gently ground, using an agate pestle and mortar, and packed in a sample planchette. X-ray diffraction data are collected using a computer-controlled STOE diffractometer with diffracted-beam graphite monochromator; $CuK_{60}$ radiation; X-ray generator at 40 kV/37mA; scan range 1°–70° in $2\theta$ at a rate of 0.04/step and counting time 4 seconds/step.

The X-ray diffraction pattern has a major spacing of 8.597 Å ($2\theta=10.28°$) inconsistent with any known crystal form of calcium malate, calcium malate hydrate, malic or maleic acids, calcium hydroxide or calcium oxides in the JCPDS International Centre for Diffraction Data, 1601 Park Lane, Swarthmore, Pa., 19081 (formerly Joint Committee on Powder Diffraction Standards) reference files.

EXAMPLE XVII

Using the procedure of Example I at water content ranging from about 70% to about 75% by weight of the reaction mixture, a study of calcium/maleate ratios is undertaken. The optimum combinations of high improved yield of malate and easily handled product are obtained at calcium/maleate ratios greater than 1.3:1 but less than about 1.7:1, especially at ratios of about 1.5:1.

EXAMPLE XVIII

Using the procedure of Example 1 and varying the water content of the reaction mixtures from about 40% to about 70% by weight, improved results, especially in that reduced fumarate byproduct levels are obtained, occur when the water content is from about 50% to about 65 wt. %. As illustrated at calcium/maleate mole ratio of about 1.2:1, fumarate byproduct levels rise significantly at water contents below about 50% and above about 65%.

EXAMPLE XIX

A procedure similar to that of Example 1 is employed, except that calcium carbonate is used to partially neutralize a solution of maleic acid; $CO_2$ evolution is complete prior to addition of calcium hydroxide in an amount selected to provide the same overall calcium/maleate and excess hydroxide: maleate ratios as used in Example I. Yields of malate similar to those of Example I are obtained.

The modified procedure demonstrates that calcium may be recycled as the carbonate and used in a pre-neutralizing step in the instant invention.

EXAMPLE XX

A study is undertaken of the impact of varying ratios of magnesium, (up to and including total replacement of the calcium hydroxide by magnesium, used as the hydroxide), to calcium in a procedure otherwise similar to that of Example I. Surprisingly, low levels of magnesium hydroxide give unexpected improvements in yield and give a unique granular product somewhat finer than that of Example XV. In one example, embodiment 3, Table 1, using 1.45 moles $Ca(OH)_2$ and 0.05 moles $Mg(OH)_2$ per mole maleate, a reaction temperature of about 160° C., a reaction time of about 6 hours, a maximum pressure of about 82 psig (0.57 MPa) and a water content of about 70%, malate yield of 99.2% is obtained. Corresponding levels of 2,2'-oxodisuccinate, fumarate and maleate are 0.2%, 0.6% and 0% respectively.

EXAMPLES ILLUSTRATING 2,2'-OXODISUCCINATE PRODUCTION

EXAMPLE XXI

Dry, granular "calcium malate" prepared according to the procedure of any one of Examples I–XV (excluding VI and VII) is finely ground using a pestle and mortar and converted to 2,2'-oxodisuccinate as follows. Taking the product of Example I for the purposes of illustration, 66.24 g (equivalent to 0.3 moles content of calcium malate and 0.15 moles content of $Ca(OH)_2$) of the ground material, 34 cm$^3$ $H_2O$. and 38.8 g, (0.48 moles) NaOH as 50% aqueous solution, (Fisher) are mixed together in a glass or stainless steel reaction vessel equipped with a stirrer, reflux condenser and heating oil bath. Powdered calcium hydroxide (2.44 g, 0.33 moles, Aldrich) is mixed in. The reaction vessel is heated, with stirring, to a temperature of about 70°–80°

C.; at which point a milky or chalky suspension is observed. Crushed, powdered maleic anhydride (36.5 g, 0.37 moles, Aldrich) is added over 5-10 minutes in small portions. Though the reaction is exothermic and may briefly reach temperatures close to reflux temperature, good stirring and thermostatting of the heating bath ensures that the mixture equilibrates rapidly to the 70°-80° C. range. During the last 3 minutes of maleic anhydride addition, a light amber homogeneous mixture, substantially clear to the eye, is formed. For best yields (assuming that the maturation process illustrated in Example XXII hereinafter is not used), the reaction is continued for a reaction time of from about 5 to 6 hours, this time being measured from completion of the maleic anhydride addition. The organic composition of the crude product corresponds to a 2,2'-oxodisuccinate content based on HPLC peak areas (Distribution Analysis) of about 74.5%, 9.7% malate, 9.5% maleate and 6.3% fumarate are copresent. Higher 2,2'-oxodisuccinate levels and lower fumarate levels are obtained in an analogous preparation based on product of Example XX having low levels of magnesium present.

EXAMPLE XXII

The procedure of Example XXI is reproduced, with the single exception that as soon after completion of the maleic anhydride addition as the homogeneous reaction mixture is formed, the mixture is cooled to about 30°-50° C. The mixture is maintained at the new, lower temperature for a period of from about 8 hours to about 21 days. HPLC analysis now gives the following results: 88.0% 2,2'-oxodisuccinate; 3.0% maleate; 3.0% malate and 6.0% fumarate.

EXAMPLE XXIII

A procedure similar to that of Example I is used, with the following reactants:
 0.9 moles maleic anhydride,
 0.1 moles fumaric acid,
 1.3 moles Ca(OH)$_2$.

The water content is about 70%, reaction temperature (oil bath) is about 185° C. and reaction time is about 6 hours. A fine granular suspension containing by way of organic components (as analyzed by HPLC) 99.0% malate, 0.5% 2,2'-oxodisuccinate, 0.5% fumarate and 0% maleate is obtained. The inorganic composition is as determined on the basis of the reactants used.

EXAMPLE XXIV

Conversion of product of Example XXII to tetrasodium 2,2'-oxodisuccinate

The reaction product mixture of Example XXII is treated with excess aqueous NaHCO$_3$/Na$_2$CO$_3$ giving a mixture having a pH of about 10. This is heated for about 4 hours at 70° C. with stirring, producing tetrasodium 2,2'-oxodisuccinate and inorganic precipitate which is separated by filtration. The solution of product is conventionally dried.

EXAMPLE XXV

Conversion of product of Example I to malic acid

The product of Example I is acidified with excess aqueous H$_2$SO$_4$, liberating malic acid.

EXAMPLE XXVI

Malate-making process (a) in presence of a limited proportion of tetrasodium 2,2'-oxodisuccinate (such as may be recycled from product of process steps (b) or (c))

The procedure of Example I is reproduced using the following reactants:
 28.8 g (0.294 moles) maleic anhydride,
 3.62 g of a 28% aqueous solution of tetrasodium 2,2'-oxodisuccinate, (yielding a total of about 0.3 moles of component I), 123.9 g of added water, and 33.3 g (0.45 moles) calcium hydroxide; with a water content of about 70% in total, a reaction temperature of about 185° C., and a reaction time of about 6 hours. A fine granular suspension is obtained. This has excellent ease of handling, and contains by way of organic components as analyzed by HPLC: 98.4% malate, 0.4% 2,2'-oxodisuccinate, 1.2% fumarate and 0% maleate. The inorganic composition is determined on the basis of the reactants used.

HPLC analytical Procedures

High Performance Liquid Chromatography (HPLC) analyses herein for maleate, malate, 2,2'-oxodisuccinate and fumarate are readily reproduced using the following conditions, by an analyst familiar with HPLC instrumentation:

Column:
 Two Supelco LC18 4.6 mm I.D.×25 cm columns equilibrated with mobile phase for about 10 days at a flow rate of about 0.2 ml/min
 Mobile Phase: 0.01–0.04N H$_2$SO$_4$ in distilled/deionized water. The sulfuric acid concentration is adjusted in dependence of the age of the columns to give separation of each of the organic species analyzed.
 Flow Rate: 1 ml/min
 Pump: A single Waters 6000A or 510
 Injector: Waters Wisp 710, injection volume 25 ul
 Director: Refractive-Index Detector; Spectra-Physics 6040XR.
 Integrator: Waters 730 Data Module
 Sample Preparation: For distribution analysis: ca. 1 g of crude reaction mixture or of purified product/100 ml 0.1N sulfuric acid; for concentration analysis: weigh a known amount into a 10 ml volumetric flask to give a peak area that falls within the calibration curve, q.s. with 0.1N sulfuric acid. In both cases, the final solution pH is about 2.
 Calculations:
 Distribution analysis: Divide peak area for a single species; i.e., maleate, fumarate, 2,2'-oxodisuccinate, malate, by total area for all peaks. This assumes equivalent refractive index response factors for all species; the assumption is proved to be an excellent approximation by concentration analysis. Based on this assumption, the distribution analysis corresponds to the relative weight percentage of the maleate, malate, 2,2'-oxodisuccinate and fumarate analyzed.
 Concentration analysis: A direct calibration curve is made for maleic acid, malic acid, and fumaric acid for direct correlation of peak areas to concentration expressed as percentage by weight.
 The same procedure is used to determine the weight % of 2,2'-oxodisuccinate except that 1,2,3,4-butanetetracarboxylic acid (structurally similar to 2,2'-oxodisuccinate) or chromatographically pure 2,2'-oxodisuccinate is used as the calibration species. Note that use of 1,2,3,4-butanetetracarboxylic acid as a reference material assumes that 2,2'-oxodisuccinate and 1,2,3,4-butanetetracarboxylic acid have similar refractive index response factors. In all cases, a linear regression analysis is used to fit the curves.

Correspondence between the results obtained for the distribution analysis and the concentration analysis is very good for a given sample. In view of the good correspondence, the tables and text herein report only the simple distribution analysis results.

What is claimed is:

1. A process for making malate by at least one step of maintaining, in a reaction vessel at a temperature of about 120° C. or above for a time of at least 10 minutes, an aqueous reaction mixture comprising:
   I maleate, or mixtures thereof with one or more of 2,2'-oxodisuccinate, fumarate and malate;
   II divalent cations selected from calcium, magnesium and mixtures thereof; and
   III sufficient hydroxide excess to render said reaction mixture alkaline;
   whereby said malate is obtained in yields up to and exceeding 90%.

2. A process according to claim 1 using a sealed reaction vessel.

3. A process according to claim 2 using pressures in the range about 30 psig to about 150 psig.

4. A process according to claim 3 wherein said reaction mixture consists essentially of said components I, II, III and water.

5. A process according to claim 4 wherefrom said malate product is isolated as a solid salt form of said divalent cation component II.

6. A process according to claim 5 wherein component I is used in the form of maleic anhydride or maleic acid, and components II and III are simultaneously provided in the form of calcium hydroxide.

7. A process according to claim 6 using a pre-neutralizing step wherein calcium carbonate and said component I are mixed and carbon dioxide is evolved prior to sealing said reactor.

8. A process according to claim 7 using a calcium/maleate mole ratio greater than about 1.3:1 and less than about 1.7:1.

9. A process according to claim 8 using a water content of said reaction mixture in the range from about 45 to about 73% by weight.

10. A process according to claim 4 using calcium as component II.

11. A process according to claim 1 wherein said reaction mixture is substantially free from sodium or potassium cations.

12. A process according to claim 1 wherein said temperature is in the range from about 130° C. to about 220° C. and said time is from about 30 minutes to about 6 hours.

13. A process according to claim 1 using a mole ratio of components III:I in the range from about 0.6:1 to about 1.4:1.

14. A process according to claim 13 using a mole ratio of components II:I greater than about 1.3:1 and less than about 1.7:1.

15. A process according to claim 14 wherein said component I consists essentially of from about 20% to about 100% maleate, from 0% to about 50% fumarate, from 0% to about 50% 2,2'-oxodisuccinate and from 0% to about 50% malate.

16. A process according to claim 15 using from about 0.8 to about 1.0 mole fraction calcium, magnesium or mixture thereof and from 0 to about 0.2 mole fraction sodium, potassium or mixture thereof.

17. The product of a process according to claim 1, comprising, on a dry weight basis, based on malate and maleate and 2,2'-oxodisuccinate and fumarate, from about 70% to about 99.5% malate, from 0% to about 30% fumarate, from 0% to about 30% 2,2'-oxodisuccinate and from 0% to about 30% maleate.

18. A process according to claim 1 using recycle of a portion of said component I.

19. A process for the manufacture of malic acid according to the process of claim 1, followed by an acidification step.

20. A process for the manufacture of 2,2'-oxodisuccinate as the sodium salt, characterized in that said process comprises at least one step (a) which is the malate-forming process of claim 1, followed by at least one step (b) of reacting the malate-containing product thereof with freshly added maleate.

21. A composition of matter comprising malate and calcium, said composition comprising a major crystalline component having a characteristic d-spacing of 8.597 Å ($2\theta = 10.28°$).

22. An aqueous alkaline process for obtaining malate in a solid, alkaline, calcium or mixed calcium/magnesium salt form by the steps comprising, in sequence:
   1. reacting maleic anhydride or maleic acid and calcium carbonate to form a mixture;
   2. permitting carbon dioxide to evolve;
   3. rendering said mixture alkaline using calcium hydroxide or mixture thereof with magnesium hydroxide; all provided that said reactants are used at a (calcium+magnesium): maleate molar ratio in the range from greater than about 1.3:1 to less than about 1.7:1, a calcium:magnesium mole ratio in the range from about 1.00:0.00 to about 0.80:0.20, a water content in the range from about 45% to about 73% and an excess of hydroxide of from about 0.6 to about 1.4 moles per mole of maleate used; and
   4. reacting said mixture in a sealed vessel at temperatures in the range from about 140° C. to about 190° C. for a period of from about 0.5 to about 6 hours.

23. A process according to claim 22 using a fumarate-containing maleate reactant in said step 1 to the extent of not more than about 0.2 moles of fumarate being present per mole of said maleic anhydride or maleic acid added in each cycle.

24. A process for forming 2,2'-oxodisuccinate, said process having at least one step (a):
   maintaining, in a sealed reaction vessel at temperatures in excess of about 120° C. for a time of at least 10 minutes, an aqueous reaction mixture comprising:
   I maleate, or mixtures thereof with one or more of 2,2'-oxodisuccinate, fumarate and malate;
   II divalent cations selected from calcium, magnesium and mixtures thereof;
   III sufficient hydroxide excess to render said reaction mixture alkaline; followed by a step (b):
   reacting the malate-containing product of step (a) together with maleate and solubilizing monovalent cations selected from sodium, potassium and mixtures thereof in aqueous alkaline media at temperatures in the range from about 65° C. to about 85° C.

25. A process according to claim 24 also having a step (c) which comprises maintaining the mixture formed in step (b) at a temperature in the range from about 20° C. to about 60° C. for a period of from about 6 hours to about 21 days, and optionally a step (d) of conventionally converting the 2,2'-oxodisuccinate-containing product of steps (b) or (c) to sodium salt form.

* * * * *